(12) United States Patent
Anderson et al.

(10) Patent No.: US 8,007,429 B2
(45) Date of Patent: Aug. 30, 2011

(54) VESSEL OCCLUSIVE DEVICE AND METHOD OF OCCLUDING A VESSEL

(75) Inventors: David W. Anderson, Brooklyn Park, MN (US); Gerald W. Timm, Minneapolis, MN (US)

(73) Assignee: GT Urological, LLC, Minneapolis, MN (US)

( * ) Notice: Subject to any disclaimer, the term of this patent is extended or adjusted under 35 U.S.C. 154(b) by 591 days.

(21) Appl. No.: 12/166,664

(22) Filed: Jul. 2, 2008

(65) Prior Publication Data

US 2009/0012351 A1 Jan. 8, 2009

Related U.S. Application Data

(60) Provisional application No. 60/958,157, filed on Jul. 5, 2007.

(51) Int. Cl.
*A61F 2/02* (2006.01)
(52) U.S. Cl. ........................................................ 600/30
(58) Field of Classification Search .............. 600/29–31, 600/37; 606/151, 157
See application file for complete search history.

(56) References Cited

U.S. PATENT DOCUMENTS

| | | | |
|---|---|---|---|
| 3,863,622 A | 2/1975 | Buuck | |
| 3,903,894 A | 9/1975 | Rosen et al. | |
| 4,118,805 A | 10/1978 | Reimels | |
| 4,222,377 A | 9/1980 | Burton | |
| 4,412,530 A | 11/1983 | Burton | |
| 4,878,889 A | 11/1989 | Polyak | |
| 4,938,760 A | 7/1990 | Burton et al. | |
| 4,994,020 A | 2/1991 | Polyak | |
| 5,509,888 A | 4/1996 | Miller | |
| 5,518,504 A | 5/1996 | Polyak | |
| 5,704,893 A | 1/1998 | Timm | |
| 5,888,188 A | 3/1999 | Srougi et al. | |
| 6,074,341 A | 6/2000 | Anderson et al. | |
| 6,117,067 A | 9/2000 | Gil-Vernet | |
| 6,463,935 B1 | 10/2002 | Forsell | |
| 6,709,385 B2 | 3/2004 | Forsell | |
| 7,060,080 B2 | 6/2006 | Bachmann | |
| 2002/0111530 A1 | 8/2002 | Bakane | |
| 2005/0251182 A1 | 11/2005 | Bachmann | |
| 2006/0264697 A1 | 11/2006 | Timm et al. | |

OTHER PUBLICATIONS

International Search Report of PCT/US2008/069155, dated Jan. 30, 2009.
Written Opinion of the International Searching Authority of PCT/US2008/069155, dated Jan. 30, 2009.

*Primary Examiner* — Charles A Marmor, II
*Assistant Examiner* — Christine Hopkins
(74) *Attorney, Agent, or Firm* — Hamre, Schumann, Mueller & Larson, P.C.

(57) ABSTRACT

An implantable vessel occlusive device and method for occluding a vessel are described, for example to occlude the urethra or bladder neck. The devices and methods described utilize an occlusive member connected to a control mechanism. The occlusive member is reversibly changed from a non-occlusive condition to an occlusive condition, for example by depressing an activation button contained within a resilient, elastomeric cover surrounding the control mechanism. In the occlusive position, an initial tension is applied to the occlusive member through a tensioning suture. The tension is translated into an occlusive pressure applied to the urethra or bladder neck that is sufficient to prevent urinary leakage. The non-occlusive position can be obtained by depressing the de-activation button. The occlusive member is constructed to allow elution of drugs, such as may be required to combat infection or tissue encapsulation from its surface.

19 Claims, 12 Drawing Sheets

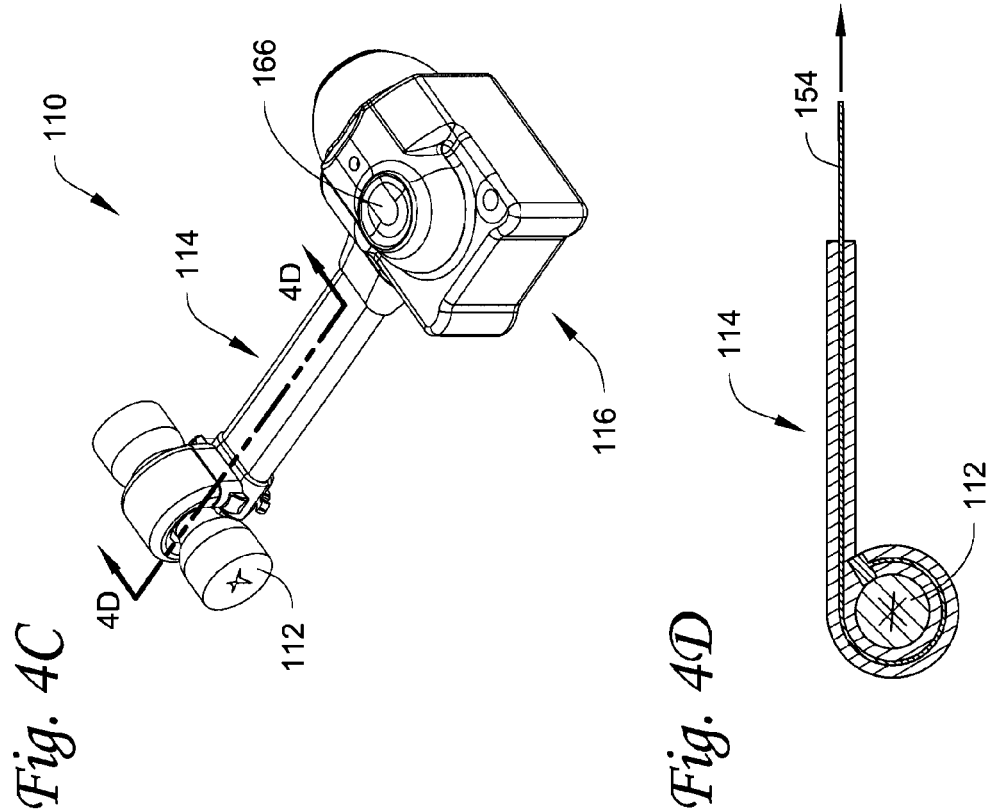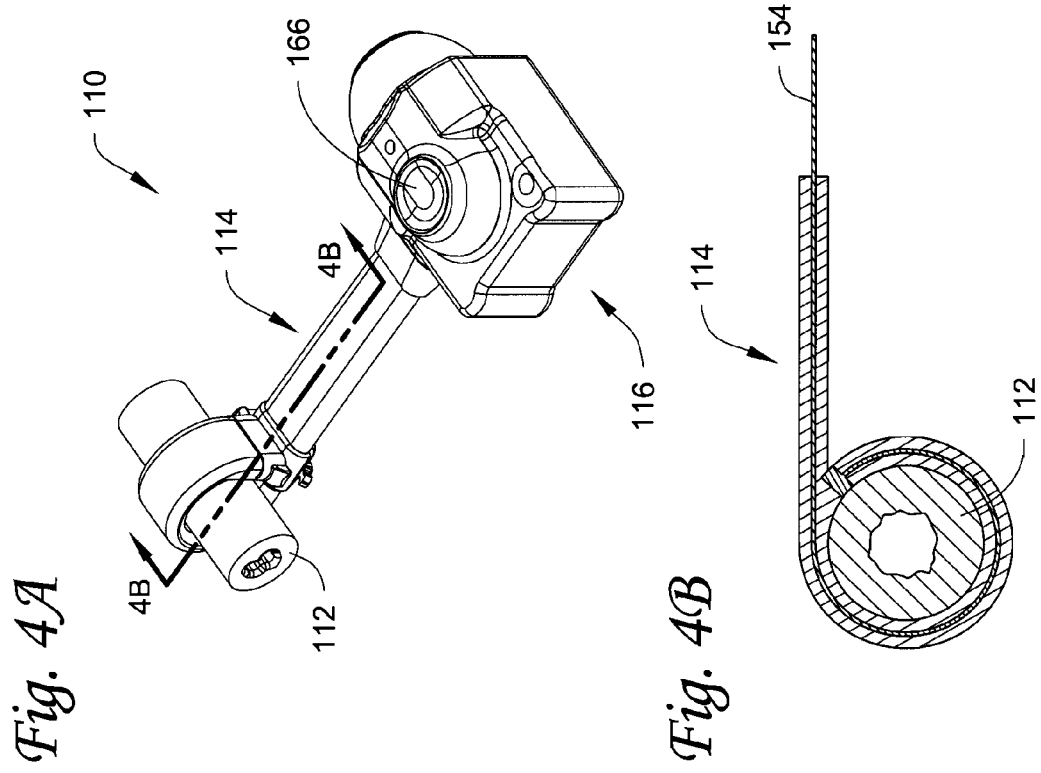

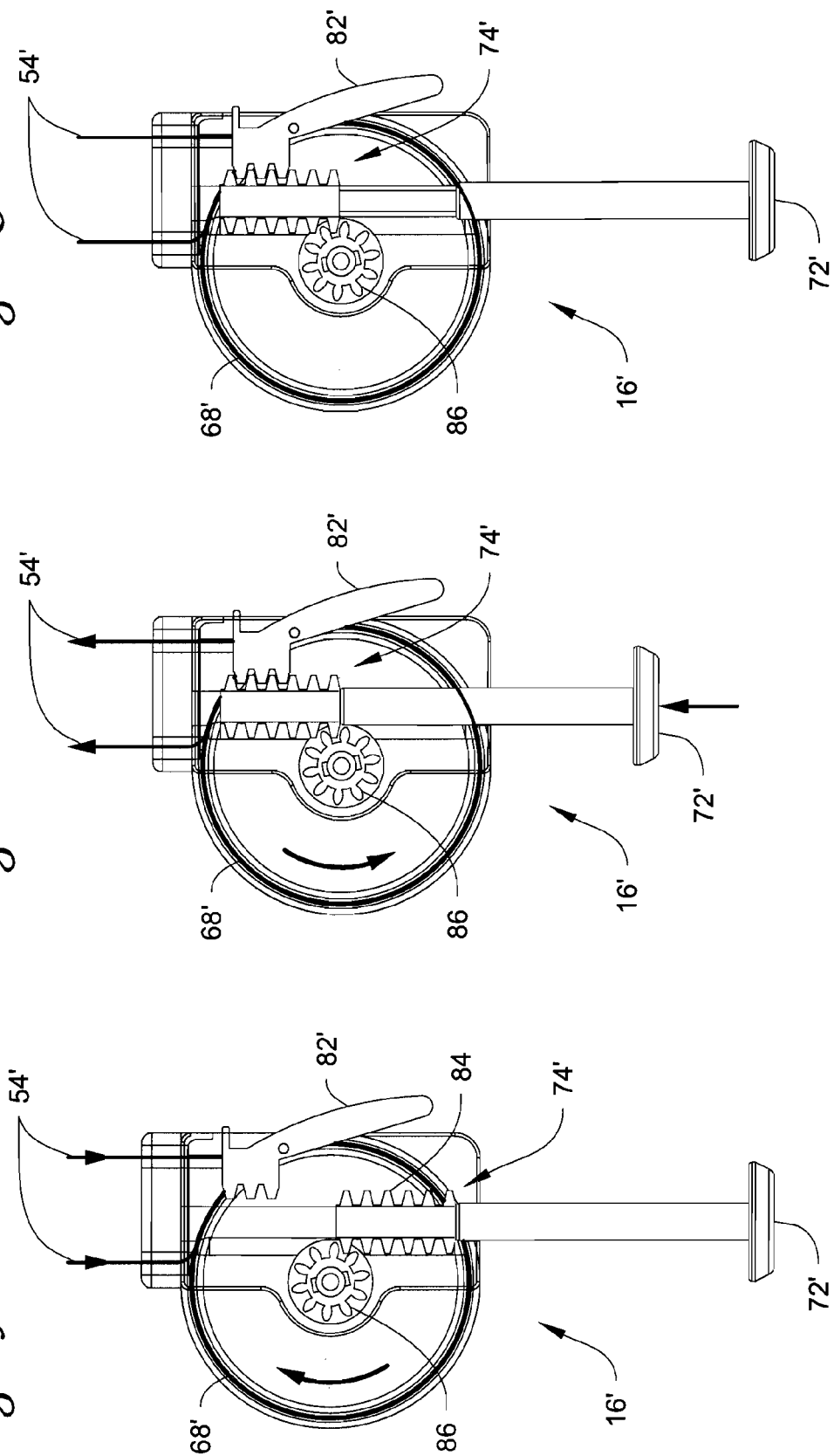

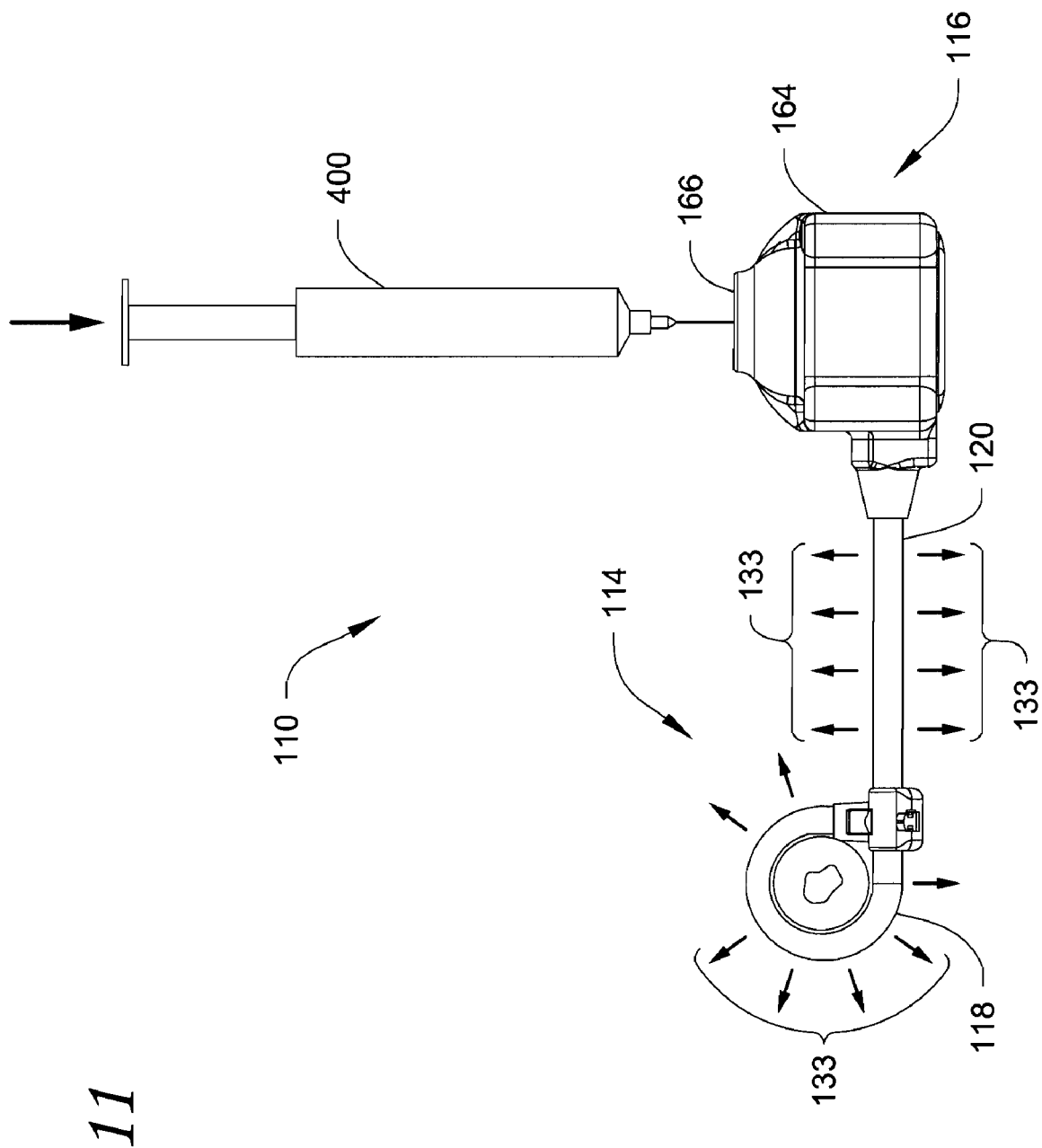

VESSEL OCCLUSIVE DEVICE AND METHOD OF OCCLUDING A VESSEL

CROSS-REFERENCE TO RELATED APPLICATIONS

The present application claims the benefit of U.S. Provisional Patent Application Ser. No. 60/958,157 entitled "TAPE MECHANICAL OCCLUSIVE DEVICE" filed on Jul. 5, 2007, which is herewith incorporated by reference in its entirety.

This invention was made with government support under SBIR Grant Number 1 R43 DK076397 01A1 awarded by the National Institutes of Health. The government has certain rights in the invention.

FIELD

This document generally relates to an occlusive device for occluding fluid conveying vessels in the body and particularly, but not by way of limitation, to a urethral occlusive device for preventing urinary incontinence.

BACKGROUND

Vessel occlusive devices are well known and commonly referred to as "artificial Sphincters". They are installed within the body to aid or replace the natural sphincter of the body. For example, men become urinary incontinent following surgeries to remove cancerous prostates. Women are often rendered incontinent due to the pelvic trauma caused during childbirth and due to a laxity of the pelvic muscles occurring due to aging. To a lesser degree, men and women may be rendered incontinent due to trauma, infection and birth defects. Urethral occlusive devices can be used to restore urinary continence to patients with urinary control problems caused by various neurological diseases, surgical procedures, spinal cord injury, etc. Other occlusive devices include those used for contracting the bowel to prevent fecal leakage, for contracting the esophagus to prevent gastro-esophageal reflux, or those used in the area of gastric banding for restricting the stomach in treatment for obesity, and occlusion of the seminal vesicles or fallopian tube to control male and/or female fertility, of which there are needs that exist for commercial devices that can be used in such applications.

In particular, devices utilizing hydraulic sphincters or cuffs described in U.S. Pat. Nos. 3,863,622; 4,222,377, 4,412,530 and 4,878,889, have been used to provide urethral occlusion. To use these types of devices, the patient squeezes a control pump, which transfers fluid from a cuff to a pressure regulating balloon. The balloon forces the fluid through a fluid restrictor and back into the cuff to reestablish an occlusive urethral pressure within 3-5 minutes. These urethral occlusive devices are complicated to implant. One problem with hydraulic sphincters or cuffs is that they often do not apply uniform pressure on the urethra. As the cuff or sphincter is inflated, it folds or changes its shape, often in a non-uniform manner, thereby exerting uneven occlusive force on the urethra. This can result in urinary leakage, urethral erosion, or the urethra tissue being worn away after extensive use.

In other examples, the American Medical Systems, Inc. AUS 800 is a commercially available, totally implantable artificial urinary sphincter. The complexity of its implantation is due to the requirement to intra-operatively fill and assemble its three components. The AUS 800 often fails due to wear in its componentry which leads to fluid leakage. Urethral atrophy and erosion sometimes occur and are suspected to be due to the crenate shape of its occlusive cuff. Post-operative infection requiring explantation of the device also is a frequent complication.

U.S. Pat. Nos. 5,704,893 and 6,074,341 discuss other types of urethral occlusive devices, which are entirely implantable artificial urinary sphincters. These artificial urinary sphincters are one-piece devices that do not require saline filling or intra-operative assembly, but where depression of a deactivation plunger, for example through the scrotal skin, causes a urethral occlusive sheath to expand and remove occlusive pressure from the urethra to allow normal urination. Depression of an activation button allows the occlusive sheath to contract and reapply urethral pressure to prevent urethral leakage. While such devices provided significant improvement in vessel occlusion, implantation in humans was impeded by growth of tough, fibrous tissue around the device, due to the natural defenses of the human body, which over time prevented expansion of the occlusive sheath.

For these and other reasons, there is a need to provide a practical and effective vessel occlusive device for aiding or replacing the natural sphincter of the body.

SUMMARY

Generally, vessel occlusive devices are described and methods for occluding a vessel or vessels that convey fluid in humans and animals are described. As one particular example, the vessel occlusive devices and methods described herein involve occluding a urethra by implanting a device into a human body for providing an incontinent patient protection against urine leakage and for providing control over the patient's voiding function.

A vessel occlusive device generally includes an occlusive member and a control mechanism for actuating the occlusive member into occluding and non-occluding positions. The occlusive member includes a pliable region configured to apply a constant force on a targeted vessel when the occlusive member is actuated in the occluding position. The occlusive member can also be configured to passively elute a solution through the occlusive member.

In accordance with the inventive principles herein, one embodiment of an apparatus for occluding a fluid conveying vessel in a body includes an occlusive member having a conduit region proximately disposed toward a proximate end and a pliable region proximately disposed toward a distal end. The occlusive member is actuatable to an occluding position and is actuatable to a non-occluding position, where an occlusive force is respectively transmitted to and released from the occlusive member. The pliable region is configured to at least partially encircle the vessel, and is configured to exert an occluding pressure on the vessel when the occlusive force is transmitted through the conduit region. A control mechanism is connected to the conduit region of the occlusive member. The control mechanism is configured to actuate the occlusive member into the occluding position and actuate the occlusive member into the non-occluding position.

In one embodiment, the occlusive member is constructed and arranged with an inner extrusion covered by an outer extrusion. The inner and outer extrusions are porous, where the outer extrusion is less porous than the inner extrusion.

In another embodiment, the occlusive member includes at least one suture lumen extending from the proximate end to the distal end, and a traction suture connected to the control mechanism and extending through the suture lumen. The control mechanism is configured to actuate the traction suture so that the occlusive member is in the occluding position and configured to actuate the traction suture so that the occlusive member is in the non-occluding position.

In another embodiment, the conduit region has a higher stiffness than the pliable region.

In one embodiment, a boot is employed to cover the control mechanism. In some examples, the boot includes a septum configured for introducing at least one fluid into the control mechanism and the occlusive member. In some examples, the fluid to be introduced includes at least one of a solution to replace air space within the control mechanism and occlusive member and a solution to provide a therapeutic effect.

In accordance with the inventive principles herein, one embodiment of a method for controlling fluid flow in a fluid conveying body vessel includes implanting a vessel occlusive device inside the body of a subject in need of controlled fluid flow through a fluid conveying vessel. The step of implanting includes surrounding at least a portion of the fluid conveying vessel, actuating the vessel occlusive device into a biased occluding position, thereby applying an occlusive force to occlude the fluid conveying vessel. The occlusive force applied to the fluid conveying vessel is released when fluid flow is to be allowed through the fluid conveying vessel. The step of releasing occlusive force includes actuating the vessel occlusive device away from the biased occluding position to a non-occluding position. The vessel occlusive device is then reactuated into the biased occlusive position when fluid flow is no longer to be allowed.

In one embodiment, a method for controlling fluid flow in a fluid conveying body vessel includes applying a constant force on the fluid conveying vessel during at least one of the implanting and the reactuating steps.

In another embodiment, a method for controlling fluid flow in a fluid conveying body vessel includes passively eluting at least one solution from the vessel occlusive device into the body to provide a therapeutic effect.

In yet another embodiment, the step of releasing the occlusive force applied to the fluid conveying vessel includes one of holding the vessel occlusive device in the occluding position and locking the vessel occlusive device in the occluding position.

BRIEF DESCRIPTION OF THE DRAWINGS

The drawings, which are not necessarily drawn to scale, illustrate generally, by way of example, but not by way of limitation, various embodiments discussed in the present document.

FIG. 4A is another perspective view of the vessel occlusive device of FIG. 2A in a non-occluding position.

FIG. 4B is a partial cross-section view of the occlusive member along line 4B-4B of FIG. 4A.

FIG. 4C is another perspective view of the vessel occlusive device of FIG. 2A in an occluding position.

FIG. 4D is a partial cross-section view of an occlusive member along line 4D-4D of FIG. 4C.

FIGS. 7A, 7B and 7C are elevational views of a gear mechanism as the control mechanism for activating and deactivating the vessel occlusive device into the occluding and non-occluding positions.

FIG. 11 is a side view of the vessel occlusive device of FIG. 2 with solutions infused into a control mechanism for elution from an occlusive member.

DETAILED DESCRIPTION

Figure 1:
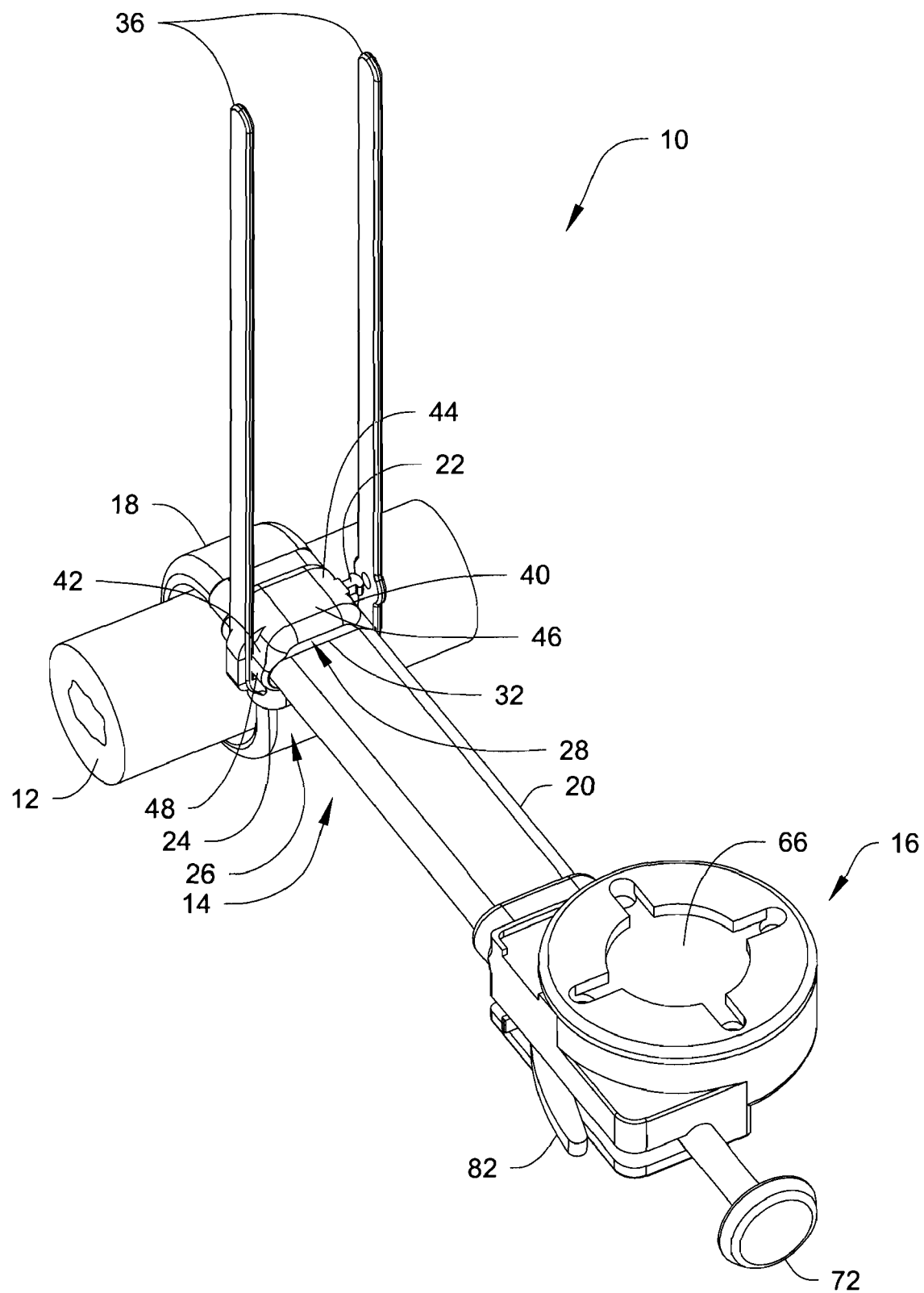
FIG. 1 is a perspective view of an embodiment of a vessel occlusive device encircling a vessel.

In the following detailed description, reference is made to the accompanying drawings which form a part hereof, and in which is shown, by way of illustration, specific embodiments in which inventive concepts may be practiced. These embodiments are described in sufficient detail to enable those skilled in the art to practice the invention, and it is to be understood that the embodiments may be combined or used separately, or that other embodiments may be utilized and that structural and procedural changes may be made without departing from the spirit and scope of the inventive concepts. The following detailed description provides examples, and the scope of the present invention is defined by the claims to be added and their equivalents.

It should be noted that references to "an," "one," or "various" embodiments in this disclosure are not necessarily to the same embodiment, and such references contemplate more than one embodiment.

The terms "above," "on," "under," "top," "bottom," "up," "down," "horizontal," and "vertical" and the like used herein are in reference to the relative positions of the vessel occlusive device, and its constituent parts, in use when oriented as in FIGS. 1-11.

In this document, the terms "occlude," "occluding," "occlusive" or "occlusion" respectively mean partially or completely occlude, partially or completely occluding, partially or completely occlusive, or partial or complete occlusion.

In this document, the terms "encircle," "surround" or "enclose" respectively mean partially or completely encircle, surround or enclose.

This document generally discusses, among other things, vessel occlusive devices and methods for occluding a vessel or vessels that convey fluid in humans and animals. As one particular example, the vessel occlusive devices and methods herein discuss applications that involve occluding a urethra by implanting a one-piece artificial device in a human body for providing an incontinent patient protection against urine leakage and for providing control over the patient's voiding function. However, it is to be understood that the present devices and methods may be employed in other areas, including, but not being limited to, fecal incontinence, gastroesophageal reflux disease, and gastric banding for weight loss, bile duct flow control, male and/or female fertility control through reversible occlusion of the seminal vesicles or fallopian tube, or to provide general occlusion or support of body vessels for other purposes. Generally, it will be appreciated that the discussion below can apply to various vessels and/or body parts that can convey fluid and may have a need to be restricted or occluded by an occlusive device. It is also to be understood that the occlusive devices described herein may include multiple pieces or components operatively connected to each other, and that they may be either partially or entirely implantable in the body of humans or animals.

Vessel occlusive devices as described herein generally include an occlusive member and a control mechanism for actuating the occlusive member into occluding and non-occluding positions. The occlusive member is configured to apply a constant force on a targeted vessel when the occlusive member is actuated in the occluding position. The occlusive member can also be configured to passively elute a solution through the occlusive member.

Methods for controlling fluid flow in a fluid conveying body vessel include implanting a vessel occlusive device inside the body of a subject in need. The step of implanting includes surrounding at least a portion of the fluid conveying vessel and actuating the vessel occlusive device to apply an occlusive force and occlude the fluid conveying vessel. The occlusive force is released when fluid flow is to be allowed through the fluid conveying vessel. The step of releasing occlusive force includes actuating the vessel occlusive device to a non-occluding position. The vessel occlusive device is then reactuated into the occlusive position when fluid flow is no longer to be allowed. In one embodiment, a constant force can be applied on the fluid conveying vessel during at least one of the implanting and the reactuating steps. In another embodiment, at least one solution is passively eluted from the vessel occlusive device into the body to provide a therapeutic effect.

FIG. 1 illustrates one embodiment of a vessel occlusive device 10. The occlusive device 10 includes an occlusive member 14 for occluding a vessel 12 and a control mechanism 16 connected to the occlusive member 14. The control mechanism 16 is operative to impart tension and release of tension on the occlusive member 14. In one embodiment, the occlusive member 14 and the control mechanism 16 form a one-piece occlusive device that does not require intra-operative assembly. The vessel occlusive devices described herein can be implanted through a single incision, which helps reduce surgical morbidity, and also helps significantly reduce the operation preparation time and the operation time of the operating room staff. It is to be understood that the occlusive devices described herein can be designed for implantation in either males or females.

FIGS. 2A-4D illustrate another embodiment of a vessel occlusive device 110 including an occlusive member 114 and a control mechanism 116. The vessel occlusive device 110 is substantially similar to the vessel occlusive device 10, except for example where the structure of the control mechanism 116 has a modified configuration and includes a cover or boot 164, which will be further described below. For ease of discussion, references of similar structure in FIGS. 1-4D are described together.

As illustrated in FIGS. 1-4D, the occlusive member 14, 114 is configured to occlude a vessel 12, 112. In one embodiment, the occlusive member 14, 114 has a tape-like configuration, and includes a greater width than its height. The occlusive member 14, 114 may have a reduced height or thickness relative to other occlusive devices, which can reduce trauma that may result from surgical dissection. By way of example, the width may vary and be in the range of approximately 0.5 to 3.0 cm, and the height may vary and be in the range of approximately 2.0 mm to 5.0 mm. As shown, the occlusive member 14, 114 includes a soft, pliable region 18, 118 configured to encircle the vessel 12, 112. The pliable region 18, 118 has a distal end 26, 126. It is to be understood that the pliable region 18, 118 can be used to completely or partially encircle the vessel in any manner so long as the vessel can be occluded or restricted.

Figure 2A:
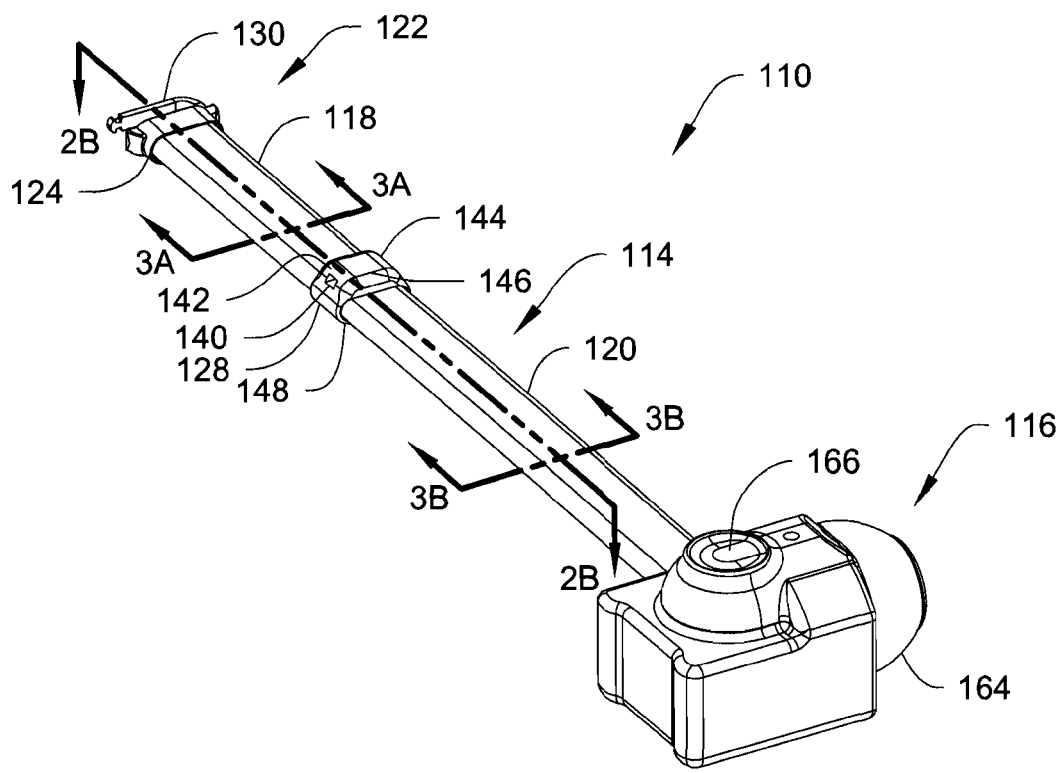
FIG. 2A is a perspective view of another vessel occlusive device in an open, deactivated state.

In one embodiment, the vessel occlusive devices 10, 110 and at least its occlusive member 14, 114, are typically shipped with the pliable region 18, 118 in an open configuration (see for example FIG. 2A). When the device 10, 110 is to be implanted, the vessel 12, 112 is then encircled by the pliable region 18, 118 with the distal end 26, 126 being attached to an attachment portion 32, 132, which is spaced away from the distal end 26, 126 and towards a proximate end of the occlusive member 14, 114. In such a configuration, the pliable region 18, 118 is held in a generally circular position as shown in FIGS. 1, 4A-4D, which allows the pliable region 18, 118 to encircle and occlude the vessel 12. The attachment portion 32, 132 can be disposed along various positions of the occlusive member 14, 114 to accommodate various vessel sizes and diameters. It will be appreciated that the attachment portion 32, 132 can be anywhere on the occlusive member 14, 114, as long as a sufficient length of the pliable member 18, 118 is left between the distal end 26, 126 and the attachment portion 32, 132 for encircling the vessel 12.

Figure 2B:
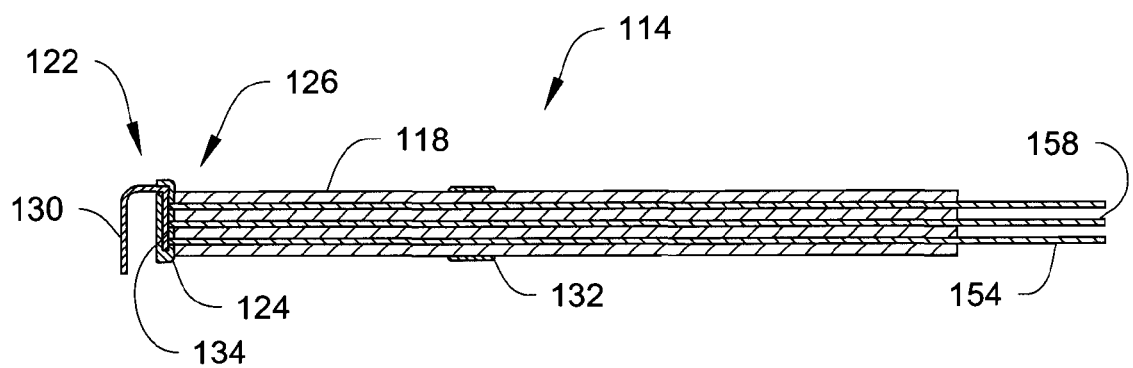
FIG. 2B is a partial cross-section view of the occlusive member along line 2B-2B of FIG. 2A.
Figure 3A:
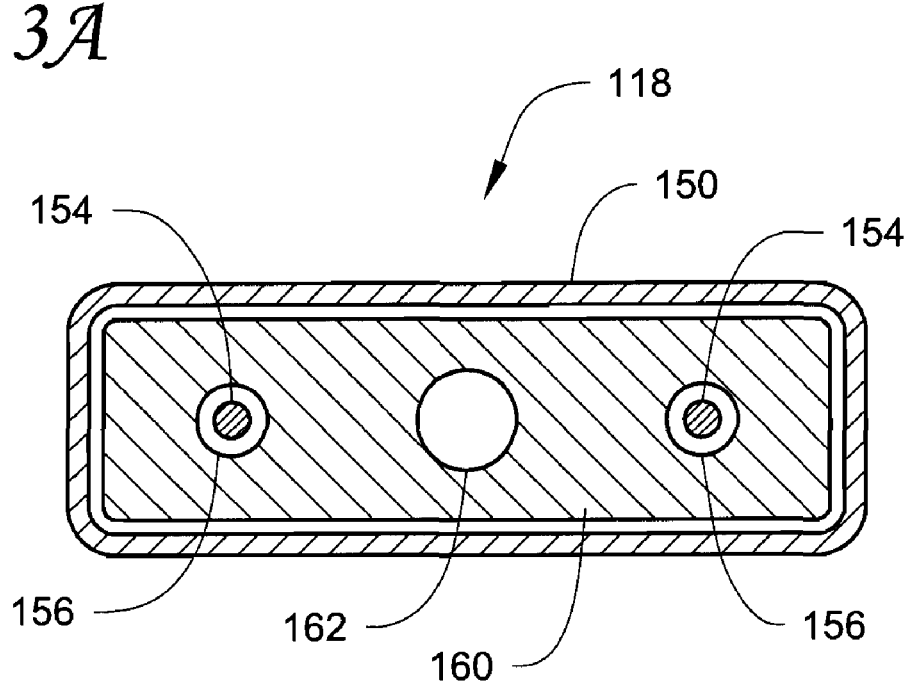
FIG. 3A is a cross-section view of a pliable region of the occlusive member along line 3A-3A of FIG. 2A.
Figure 3B:
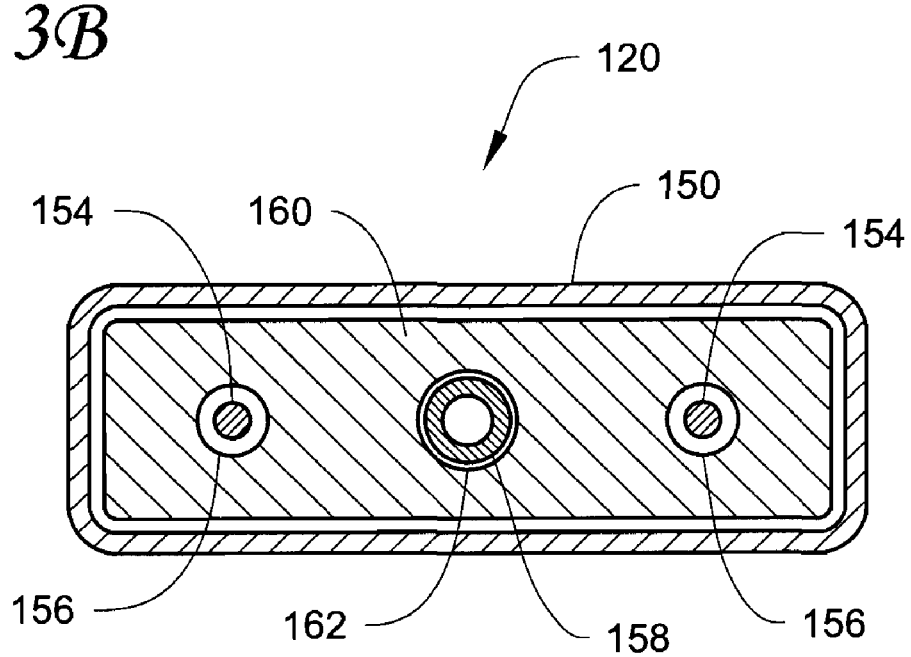
FIG. 3B is a cross-section view of a conduit region of the occlusive member along line 3B-3B of FIG. 2A.

In one embodiment, a clip-band mechanism can be used for attaching the distal end 26, 126 to the attachment portion 32, 132. The clip-band mechanism includes a clip 22, 122 formed on the distal end 26, 126 of the occlusive member 14, 114, and a band 28, 128 wrapping around the attachment portion 32, 132, where the clip 22, 122 is engageable with the band 28, 128. As shown in FIG. 2B for example, clip 122 is generally a U-shape clip including a first prong 134 and a second prong 130 having a projecting tongue-like structure. While the specific structure of clip 22 is not shown, it will be appreciated that clip 22 can have the same or similar structure as clip 122.

In one embodiment, the band 28, 128 includes a main body 46, 146 and a wrapping member 48, 148 that can wrap around the attachment portion 32, 132. In one embodiment, when the band 28, 128 is wrapping around the attachment portion 32, 132, the main body 46, 146 is located above the attachment portion 32, 132. A transverse aperture 40, 140 extends through a first side surface 42, 142 of the main body 46, 146 and a second side surface 44, 144 for receiving the second prong (e.g. 130) of the clip 22, 122.

The distal end 26, 126 includes an end cap 24, 124 that can engage the clip 22, 122 (e.g. first prong 134). In one embodiment, the first prong 134 of the 122 clip is inserted into an injection or transfer molded silicone end cap 124. An example of a suitable silicone is a silicone manufactured by Nusil, Inc. of Carpenteria, Calif.

The clip 22, 122 is configured to clip on the band 28, 128 with the second prong 30, 130 being inserted and extended through the aperture 40, 140, so that the distal end 26, 126 is clipped on and against the wrapping member 48 and 148. In such a configuration, the clip 22, 122 is engaged with and can be locked onto the band 28, 128 so that the pliable region 18, 118 is held in a generally circular position and encircles the vessel 12 in a manner as shown in FIGS. 1, 4A-4D. It will be appreciated that the orientation of the clip 22, 122 and band 28, 128 may vary as necessary and/or desired, as long as the clip 22, 122 can connect to the band 28, 128 so as to encircle the vessel to be occluded. That is, the structure of the clip 22, 122 and the band 28, 128 is meant to be non-limiting and may be configured and arranged in any way that would allow the pliable region 18, 118 of the occlusive member 14, 114 to bend to connect the clip 22, 122 to the band 28, 128. For example, the clip 22, 122 and the band 28, 128 may be configured and arranged so that the pliable region 18, 118 can be bent to attach to the attachment portion 32, 132 from any side, top, or bottom of the occlusive member 14, 114.

The clip 22, 122 may be manufactured from 316L stainless steel, 6A14Veli titanium, or plastics by machining, metal stamping or plastic or metal injection molding processes. As one example of a suitable material, a poly ether ether ketone (PEEK) such as manufactured by Invibio, Inc. of Greenville, S.C. can be employed.

In one embodiment, as shown in FIG. 1, tabs 36 may be attached to the end cap 24 at the time the occlusive device 10 is implanted to help position the occlusive member 14 around the vessel 12 through a surgically created channel. The tabs 36 aid in locating and holding the occlusive member 14 in place against a surface proximate and external to the vessel 12, so that the clip 22 can be connected to the band 28. The tabs 36 may be removed once the clip 22 is engaged with and locked to the band 28. In one embodiment, the tabs 36 are made of a silicone material. It will be appreciated that tabs 36 may be similarly employed with end cap 124 of vessel occlusive device 110, so as to aid in positioning the occlusive member 114 around the vessel 112.

With reference to FIGS. 3A-4D, the occlusive member 114 has a micro-porous construction intended to minimize tissue in-growth. While only the occlusive member 114 is discussed, it will be appreciated that the occlusive member 14 may be constructed and arranged as described and shown in FIGS. 2B, 3A-B, 4B, and 4D with respect to the occlusive member 114. As shown, the occlusive member 114 in one embodiment includes an outer, thin-walled layer 150 and an inner extrusion 160. The outer layer 150 can be made of a porous material, such as expanded polytetrafluoroethylene (ePTFE). The outer ePTFE layer 150 is manufactured with as thin a wall as possible, such as approximately 0.003" to 0.010" inches, to minimize its stiffness and the influence it may have on the ability of the inner extrusion 160 to expand or collapse. The porosity of the outer layer 150 has an internodal distance in a range of approximately 5-15 microns (IND) to minimize or prevent the ingrowth of tissue into its porous structure.

The inner extrusion 160 also can be made of expanded polytetrafluoroethylene (ePTFE), and can be manufactured having a porosity in a range of approximately 80-100 microns, which insures that the extrusion 160 compresses greatly when an axial load is applied. The extrusions 150, 160 can be manufactured by several companies, such as International Polymer Engineering, Inc. of Tempe, Ariz.

In one embodiment, the inner extrusion 160 includes a lumen 162 generally located in the center of the extrusion 160 and at least one suture lumen 156 generally located peripherally of the lumen 162. In one embodiment, both the lumen 162 and the suture lumen 156 extend through the entire length of the occlusive member 114. It will be appreciated, however, that the central lumen 162 may not extend through the entire length of the occlusive member 114. It is to be understood that the positioning of the lumens can be varied, depending on the specific shape of the occlusive member 114. It is also to be understood that the number of lumens can vary as desired and/or necessary, depending on for example the occlusive force to be transmitted through the suture lumens and the stiffening quality needed for a conduit region of the occlusive member 114 (discussed below).

The occlusive member 114 further includes traction sutures 154. In one embodiment, the traction sutures are affixed to the end cap 124 and extend through lumens 156 within the inner extrusion 160. Force or tension applied by the control mechanism 116 can be transmitted to the pliable region 118 through the suture 154 to put the pliable region 118 into an occluding position (FIG. 4D) and a non-occluding position (FIG. 4B), which will be further described below.

As further shown, the occlusive member 14, 114 includes a conduit region 20, 120 that connects the pliable region 18, 118 to the control mechanism 16, 116. The conduit region 20, 120 of the occlusive member 14, 114 in some embodiments is more rigid or stiff than the pliable region 18, 118. For example, the conduit region 20, 120 is made stiffer than the pliable region 18, 118 by feeding a closely-wound wire coil 158 through a portion of the lumen 162 of the inner extrusion 160 to prevent collapse. By way of example only, the coil 158 can be wound using standard coil winding techniques and may be manufactured from materials as a nickel-cobalt alloy, such as the known 316 stainless steel or MP35N®. It will be appreciated that the conduit region 20, 120 may be made with rigid, stiff properties using a variety of implementations and techniques and is not meant to be limited to the specific structure shown. As one example only, a central lumen and coil may not be employed, but where portions of the extrusions 150, 160 which correspond to the conduit region 20, 120 may be constructed and formed of a material so as to provide the needed rigidity relative to the pliable region 18, 118.

Figure 5A:
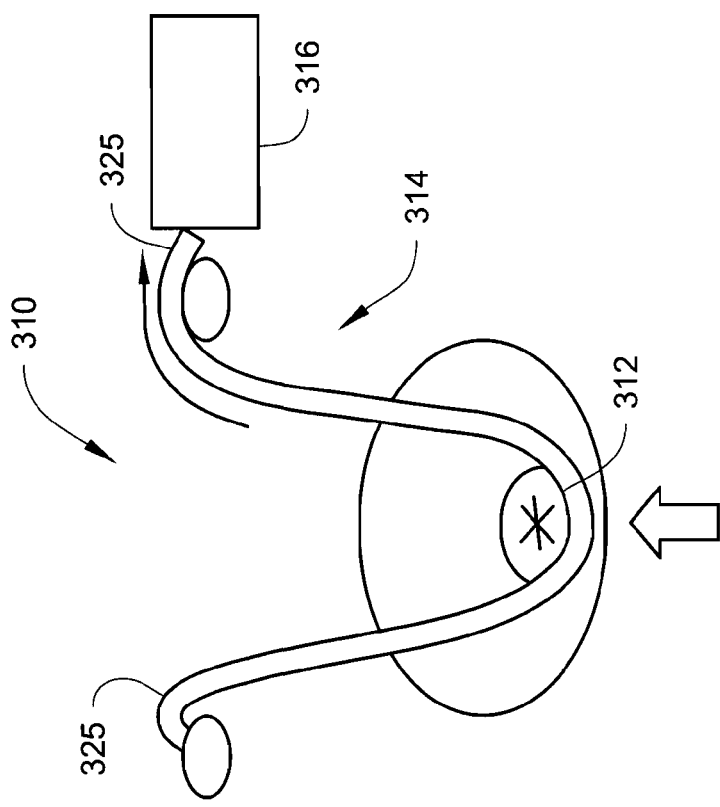
FIG. 5A is a schematic view of another embodiment of a vessel occlusive device having a sling occlusive member in a non-occluding position.
Figure 5B:
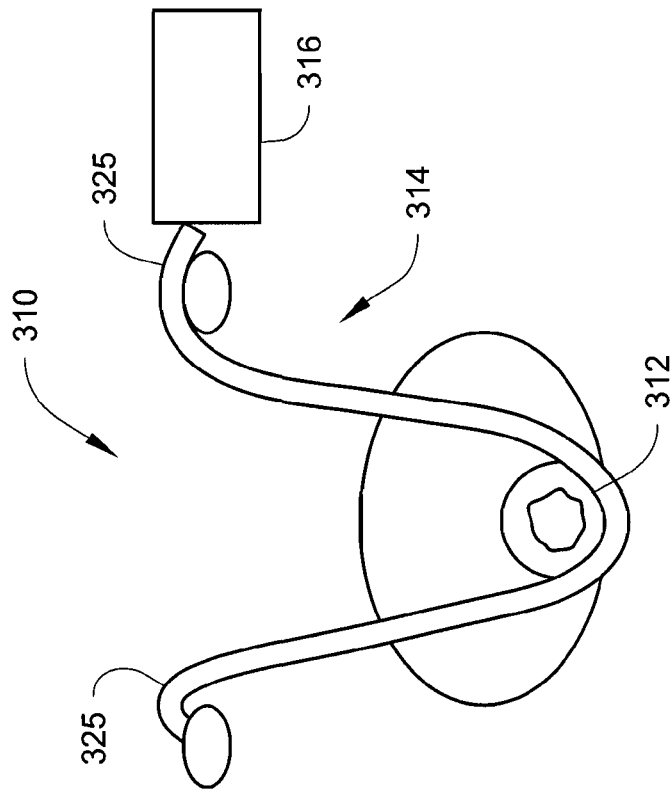
FIG. 5B is a schematic view of the vessel occlusive device of FIG. 5A in an occluding position.

With reference to FIGS. 5A and 5B, the occlusive member may also be configured to provide adjustable support to tubular body organs without completely encircling them. In one embodiment, an occlusive member 314 may be employed as a sling configuration to provide urethral support in either males or females. The degree of support may be adjusted to accommodate varying anatomical conditions and degrees of urinary incontinence. The ends 325 of the occlusive member 314 can be fixed for example to the pubic bone, or endopelvic facsia, such as by sutures or screws. The occlusive member 314 may be of a similar material and construction as occlusive members 14, 114 including the traction sutures and inner/outer extrusions, except without the clip-band and attachment portion since the occlusive member does not encircle the targeted vessel. As a load is applied to traction sutures by a control mechanism 316, the occlusive member 314 elevates the urethra, thereby compressing it from the underside and increasing the intra-urethral pressure to prevent leakage. The control mechanism 316 employed can be any of the control mechanisms described herein. As shown, the control mechanism 316 is disposed at one end of the occlusive member 314. It also will be appreciated that a control mechanism may be disposed at the other end, so that the occlusive member 314 can be elevated from either or both ends.

With further reference to FIGS. 1-4D, the control mechanisms 16, 116 are operative to impart tension on and to release tension from the occlusive member 14, 114. While certain control mechanisms described herein are shown with respect to one of the vessel occlusive devices 10, 110, it will be appreciated that the control mechanisms are not limited to any particular vessel occlusive device, and that any control mechanism described can be suitably adapted and employed for use in any of the devices herein. It also is to be understood that any of the control mechanisms described herein can be mechanically actuated, electrically actuated or mechanically-electrically actuated. Any of the control mechanisms described herein also can be encapsulated by a silicone boot (e.g. a shown in device 110 FIG. 2A). In one embodiment, the silicone boot allows access to a needle port or septum (e.g. 66) for delivering a fluid to the occlusive member (e.g. 14).

With reference to FIGS. 1 and 6A-6D, the control mechanism 16 is attached to the occlusive member 14. Traction sutures 54 extend from the occlusive member 14 and are attached to a cable and pulley system for positioning the device 10 into the occluding and non-occluding positions. As shown, pulley 68 is situated and free to rotate within the control mechanism 16. The traction sutures 54 are connected to the pulley 68.

The pulley 68 may be machined or injection molded from a host of materials including, but not limited to, ultra high molecular weight polyethylene (UHMWPE), poly etherether ketone (PEEK), titanium 6A14Veli or 316 stainless steel.

A biasing member of constant force is disposed within the center of the pulley 68. As one example, the biasing member is a coiled spring 70 disposed within the center of the pulley 68. As shown, the spring 70 in one embodiment is disposed within a circular pocket of the pulley 68 (see for example FIG. 6D). An example of a suitable coiled spring 70 is a spring manufactured by Elgiloy, which has a long history of usage in springs and implantable devices.

Figure 6A:
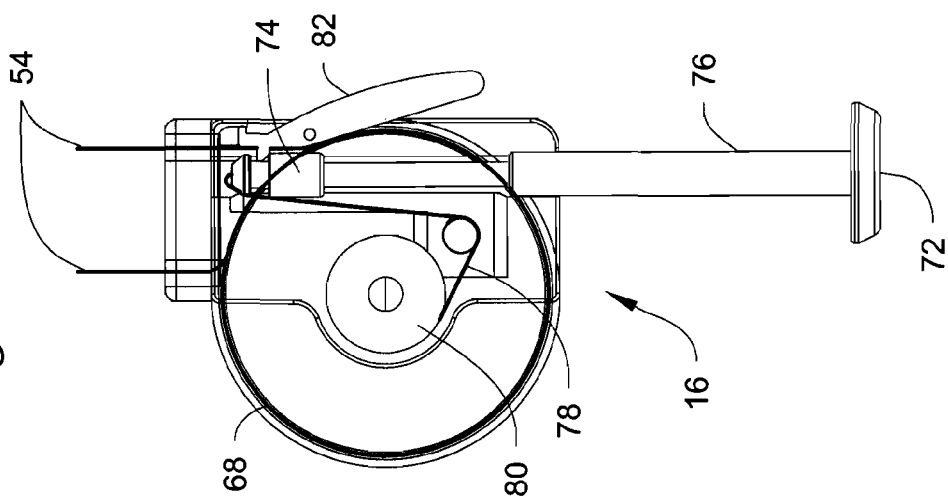
FIGS. 6A-6D are elevational views of a cable mechanism as the control mechanism for activating and deactivating the vessel occlusive device into the occluding and non-occluding positions.

In one embodiment, the coiled spring 70 is biased to apply an initial constant force or tension on the attached traction sutures 54 (see FIG. 6A). When the device 10 has been implanted, this force is transmitted to the pliable region 18 of the occlusive member 14 to initially compress the occlusive member 14 and apply occlusive pressure to the vessel 12 (i.e. the occluding position). It will be appreciated that the configuration of the occlusive member 14 and the traction sutures 54 can provide a uniform and an even occlusive pressure when the device is in the occluding position. Removal of the occlusive force to allow unobstructed urinary voiding is accomplished through counter-rotation of the pulley 68 to remove tension on the traction sutures 154 (see FIG. 6B, i.e. the non-occluding position). With the tension removed, the occlusive member 14 is free to expand due to its inherent resilience and due to vessel expansion when the vessel 12 becomes pressurized with fluid. (See also FIGS. 4B and 4D for example showing the occluding and non-occluding positions of a vessel.)

Exemplary embodiments are described and shown below which transmit force to the occlusive member and remove force therefrom. In a first exemplary embodiment shown in FIGS. 6A-D, counter-rotation of the pulley 68 is accomplished when the user depresses a plunger 72 extending outside the control mechanism 16. In one embodiment, the plunger 72 is a two-piece structure having a plunger barb 74 that can telescope into and out of a plunger barrel 76.

With further reference to FIG. 6A-6D, the control mechanism 16 includes a cable 78 beginning at the tip of the plunger barb 74 and ending around a second pulley 80. The second pulley 80 is operatively connected to the first pulley 68 and has a smaller diameter than the first pulley 68. As the plunger 72 is depressed, the cable 78 rotates the small pulley 80 and in turn, counter rotates the larger pulley 68 to release tension on the traction sutures 54 and compression of the occlusive member 14.

It is to be understood that the ratio of the two pulley diameters may be varied to maximize the degree of counter-rotation of the large pulley 68 and to minimize the axial movement of the plunger 72. Smaller plunger movements can ease the manual operation by the user. As some examples only, axial movements can be maintained in the range of approximately 0.10" to 0.50" inches. For example, initial rotation of the larger pulley 68 may be intended to provide the greatest degree of vessel 12 compression possible, for example a male or female urethra. In such a case, the larger pulley 68 can be initially rotated or biased into the compression or occluding position to provide approximately 2.5 cm to 4.0 cm linear take up of the traction sutures 54. To account for such initial linear take up of the traction sutures 54, the pulley, cable, and plunger structure can be suitably modified so that a suitable counter rotation can be achieved to release tension on the traction sutures 54.

Figure 6B:
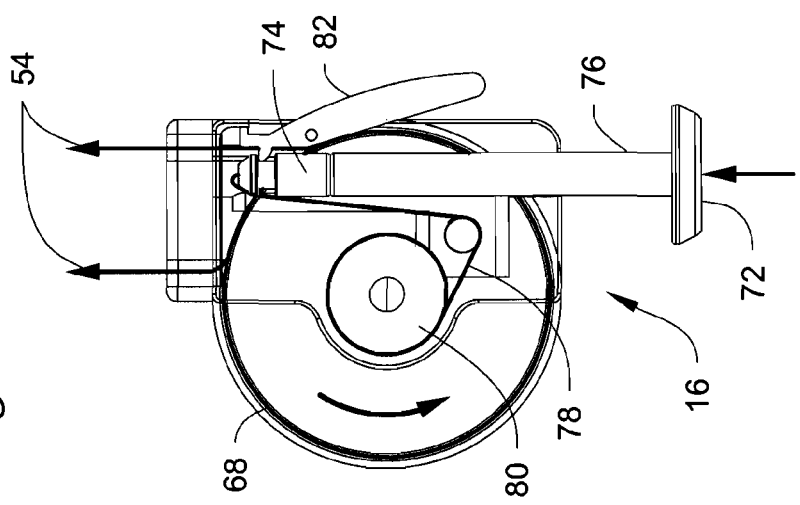

The user has the option of depressing and holding the plunger 72 in its depressed state while urinating or depressing the plunger 72 until it locks into a fully depressed condition as shown in FIG. 6B. In this fully depressed condition, the plunger 72 engages a biased lever 82 having a detent, which can lock the plunger 72 in place when the plunger 72 is extended past the detent of the lever 82. A resilient silicone rubber cover or boot (not shown) can encapsulate at least the plunger barrel 76 and help return the plunger barrel 76 to its normally extended position when the user removes manual force (see FIG. 6C). The plunger barb 74 will remain locked by the lever 82 until the user manually depresses the lever 82 to release the plunger barb 74 from the detent. When the plunger barb 74 is released, it can return to its extended position under the influence of the load of the coil spring 70 on the cable 78.

Figure 6C:
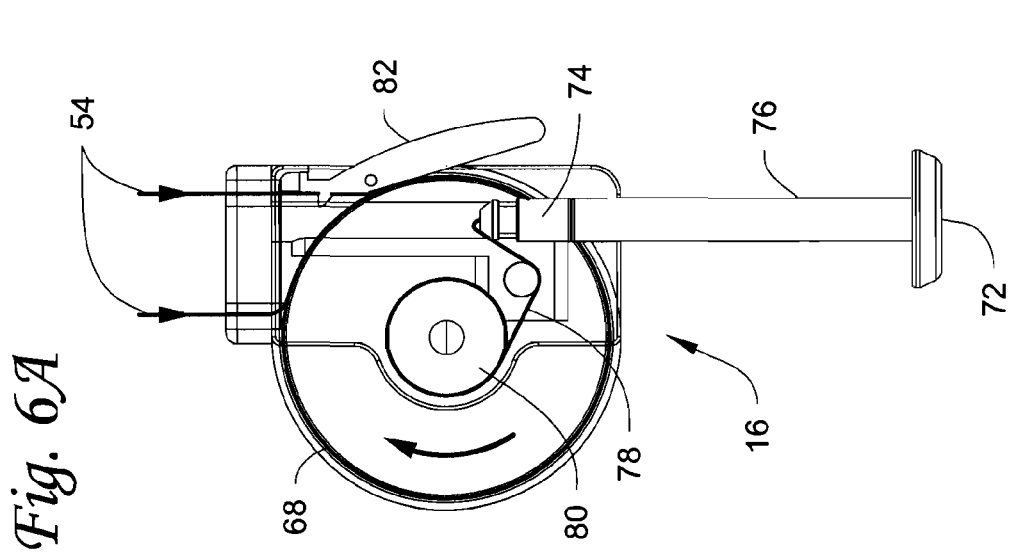
Figure 6D:
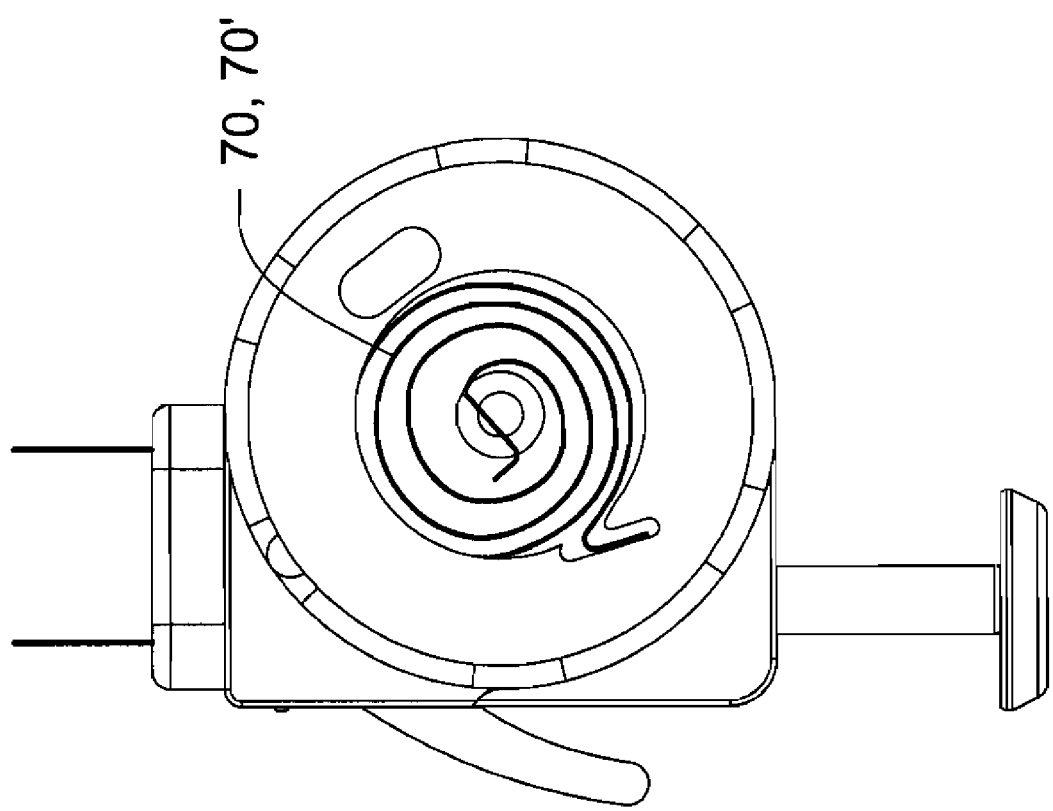

In a second exemplary embodiment for transmitting force to and from the occlusive member, FIGS. 7A-C show a control mechanism 16' with a gear and pulley system. The cable 78 and small pulley 80 shown in FIGS. 6A-C are replaced with a geared tip 84 on the plunger barb 74' and a spur gear 86 operatively connected to the pulley 68'. Movement of the plunger 72' and pulley 68' is substantially similar to the embodiment shown by FIGS. 6A-C. When the plunger 72' is depressed, the geared plunger barb 84 engages and rotates the spur gear 86, which counter rotates the pulley 68'. The geared plunger barb 84 can be locked with the detents of the lever 82' when the plunger barb 84 engages the lever 82, so as to hold the plunger barb 84 and pulley 68' in a counter-rotated condition (i.e. non-occluding position). The plunger barb 84 can be released when the lever 82' is manually depressed, and the pulley 68' is again free to rotate under the influence of the load from the spring 70', thereby re-establishing vessel occlusive pressure.

Figure 8A:
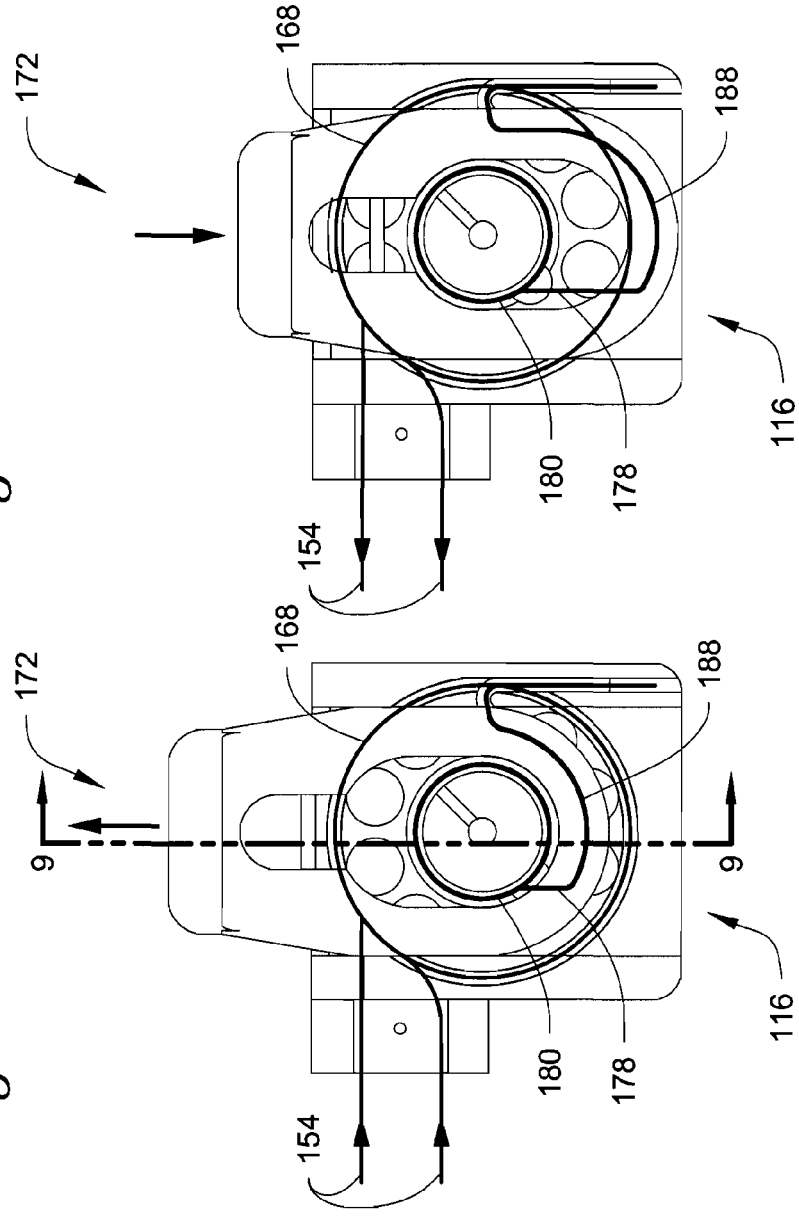
FIGS. 8A-8C are elevational views of a radiused base plunger in a cable mechanism used as the control mechanism for activating and deactivating the vessel occlusive device into the occluding and non-occluding positions.
Figure 8B:
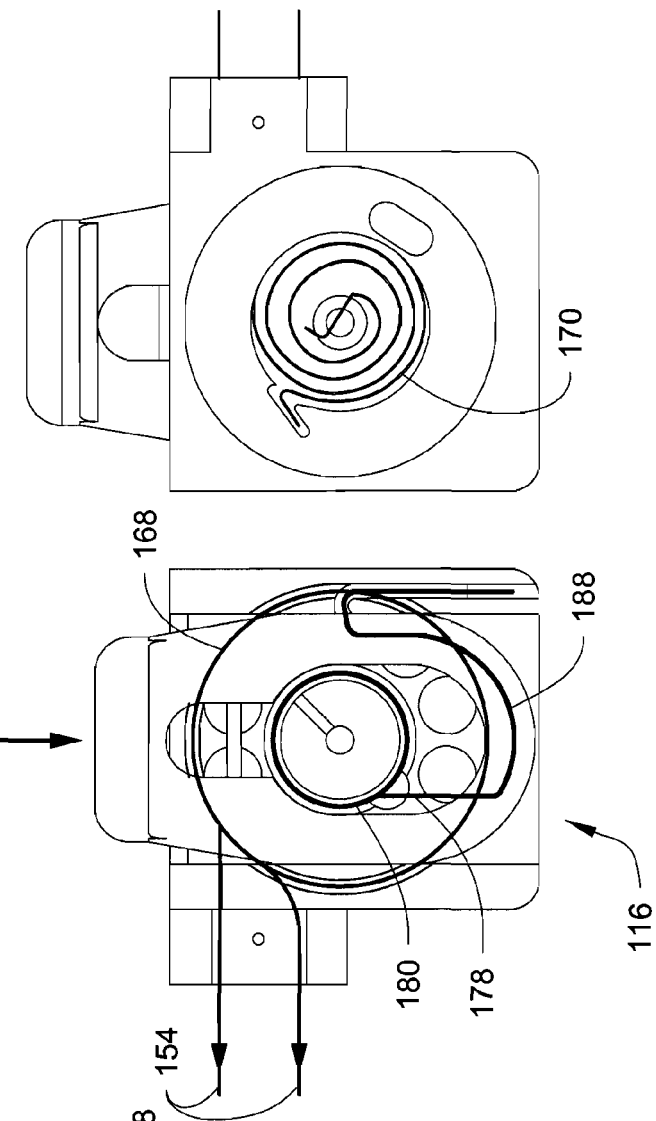
Figure 8C:
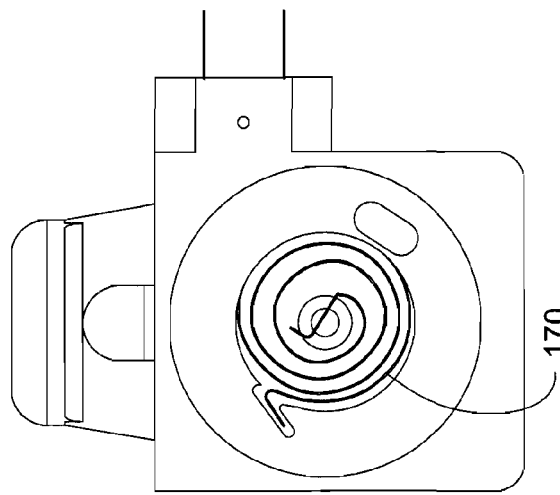

In yet another embodiment for transmitting force to and from the occlusive member, FIGS. 8A-8C show another cable and pulley system such as for control mechanism 116. The cable and pulley system has many similarities as described in the embodiment shown in FIGS. 6A-C, but with some differences. A pulley 168 can be biased by a coil spring 170 (see for example FIG. 8C) that imparts initial tension on the traction sutures 154 and puts an occlusive member (e.g. 14, 114) in an occluding position. As shown, the spring 170 in one embodiment is disposed within a circular pocket of the pulley 168 (see for example FIG. 8C). Counter-rotation of the pulley 168 is accomplished when the user depresses a plunger 172 that extends out of a main body of the control mechanism 116. A cable 178 wraps around the small pulley 180 at one end and also is generally disposed around a radiused base 188 of the plunger 172. As shown, the distal end of the cable 178 can be fixed on the body of the control mechanism 116 (see lower right hand side of FIGS. 8A-B). The cable 178 can be pulled by the radiused base 188 of the plunger, when the plunger 172 advances. The small pulley 180 rotates when the cable 178 is pulled thereby rotating the pulley 168. Thus, as the plunger 172 advances, a distance that the cable 178 is pulled can be doubled relative to a distance the plunger 172 advanced. In such a configuration, relatively shorter displacement is required to counter-rotate the pulley 168, so as to sufficiently remove tension on the occlusive member and remove occlusion from the vessel 112 (i.e. non-occluding position). The control mechanism 116 also can be made more compact as less space and less axial movement are needed for the plunger 172.

Figure 9A:
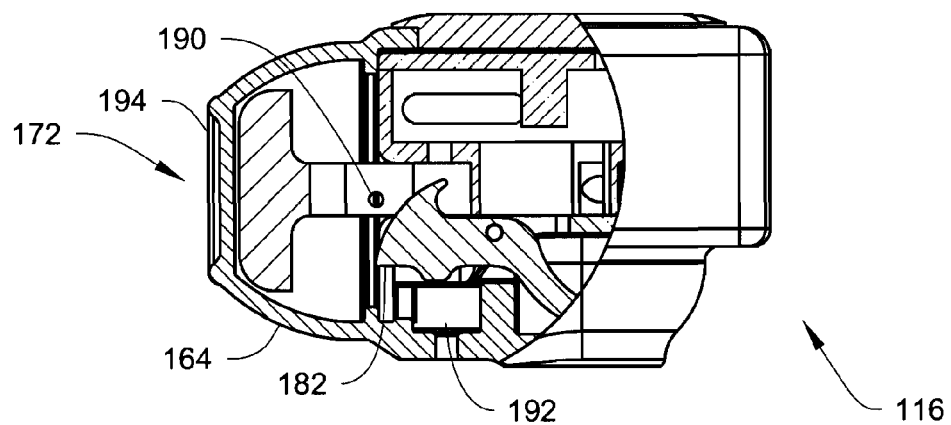
FIGS. 9A, 9B and 9C are sectional views of the control mechanism in FIGS. 8A and 8B and including a plunger dome as part of the cover of the control mechanism.
Figure 9B:
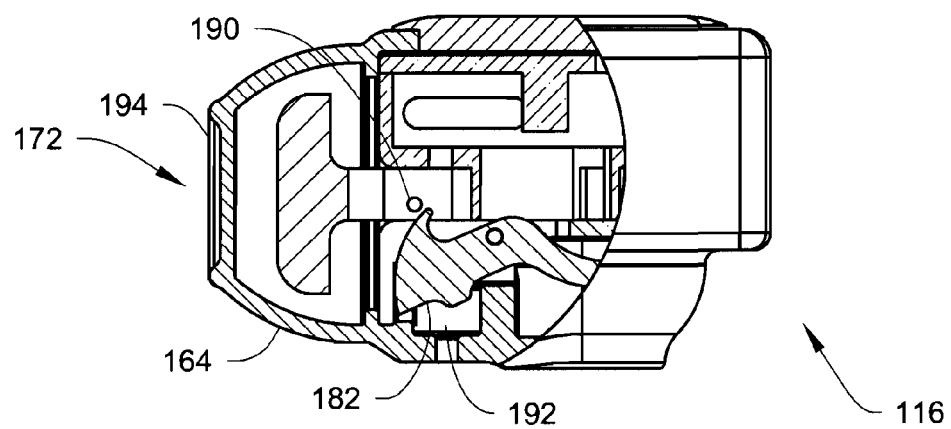
Figure 9C:
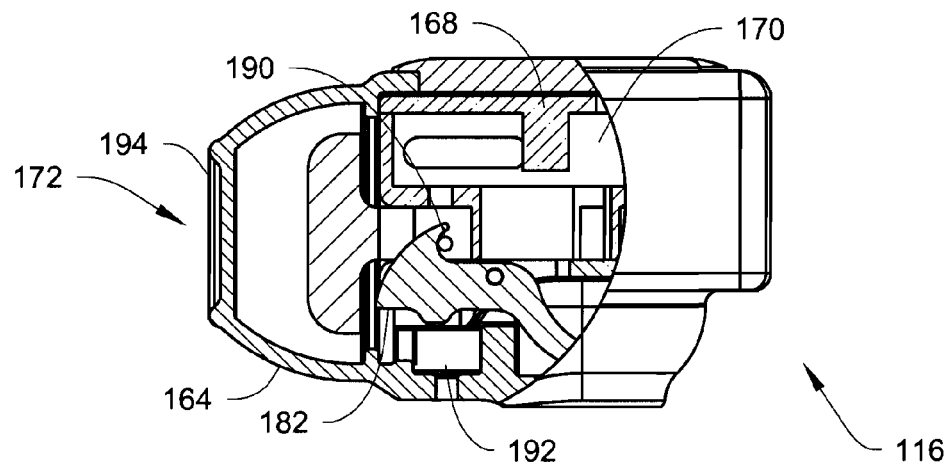

FIGS. 9A, 9B and 9C show side sectional views of the control mechanism 116 of FIGS. 8A. Particularly, an embodiment of a boot or cover for at least the plunger is illustrated, and a lever 182 and lock are also illustrated. It will be appreciated that the boot or cover may encapsulate the control mechanism 116, and it will be appreciated that a similar cover may be employed for any of the control mechanisms (e.g. 16, 16') described herein.

As shown, when the plunger 172 is depressed to its full extent, a pin 190 disposed on the plunger 172 engages a detent of the lever 182, which locks the plunger 72 and prevents it from returning to its original extended position. The lever 182 can be biased by a spring 192. In one embodiment, the spring 192 is disposed between the lever 182 and a generally flexible silicone rubber cover or boot 164 substantially surrounding the control mechanism 116. As the plunger 172 is depressed, a plunger dome 194 of the flexible silicone boot 164 deforms with the force applied to it, but can also return to its original shape when the force is removed. In the configuration shown, the occlusive member can be locked in a state which does not compress the vessel 112 and can be released from a locked position to return compression to the vessel 112. The resilient plunger dome 194 can help prevent tissue from forming around the device when it is implanted, and can help prevent movement of the plunger 172 from being restricted.

When a user desires to return to a continent state with the vessel compressed, the lever 182 is depressed so that the pin 190 of the plunger 172 can disengage from the detent of the lever 182. Such an action allows the plunger 172 to return to an extended position, for example as a result of the bias of the spring 170.

Figure 10:
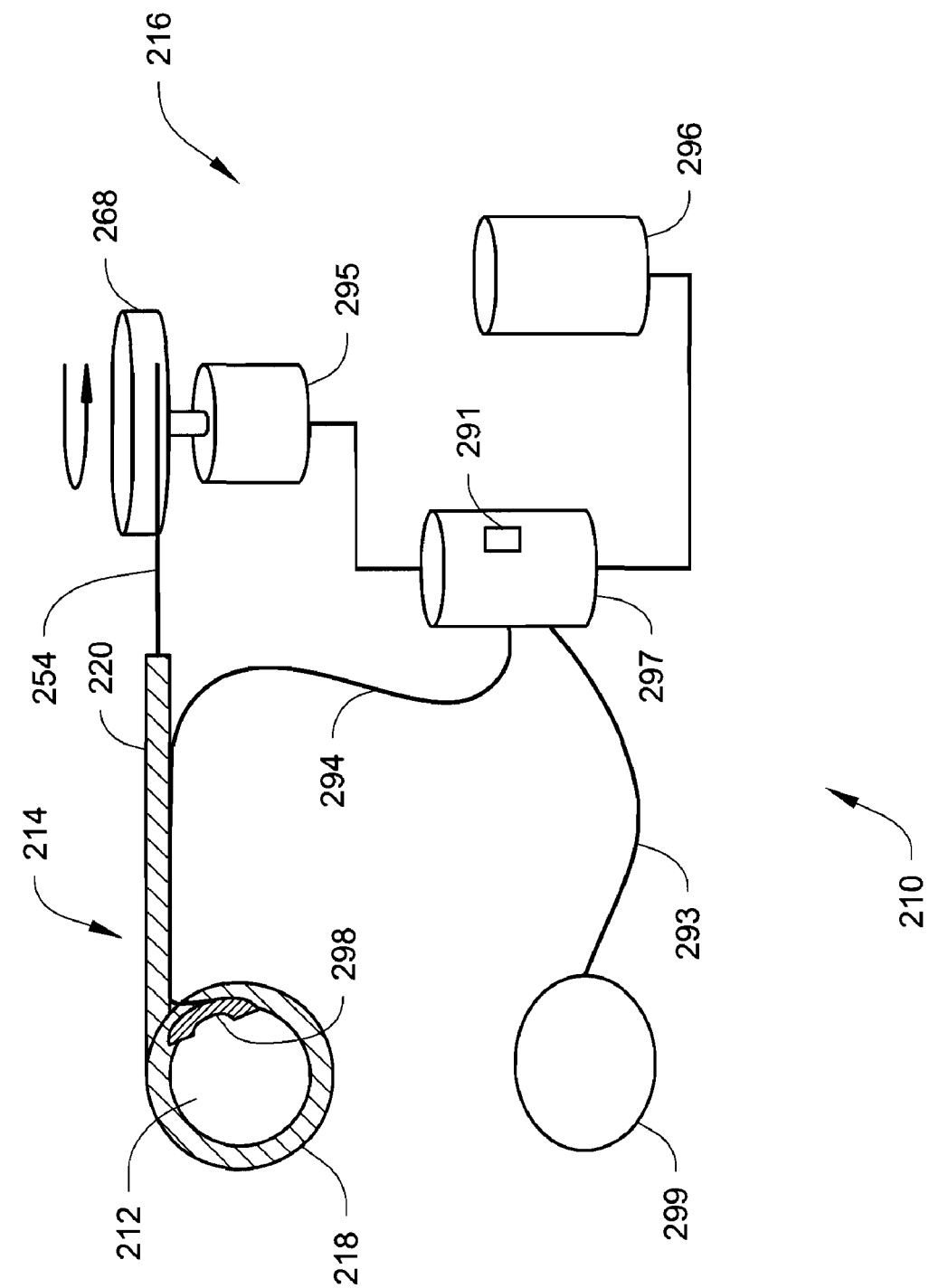
FIG. 10 is a schematic view of a motorized vessel occlusive device.

With reference to FIG. 10, a vessel occlusive device 210 includes an occlusive member 214 and another embodiment for a control mechanism 216 that may be configured and arranged as a closed loop, electromechanical, servo-control system. A vessel 212 can be constricted by a pliable region 218 of the occlusive member 214 such as described above. The occlusive member 214 may further include a conduit region 220 configured and arranged such as described above.

In one embodiment, the control mechanism 216 includes a pulley 268 operatively connected to an electric motor 295. The electric motor 295 is operatively connected to a micro-processor based control 297 having a power supply 296. A separate vessel pressure sensing element 298 is operatively connected to the micro-processor based control 297, for instance through a wire 294. A pressure sensing element 299, such as for example the abdomen, is operatively connected to the micro-processor based control 297, for instance through a wire 293. In the embodiment shown, the electric motor 295 can turn the pulley 268, which in turn takes up and applies a load to a traction suture 254, to compress or constrict the occlusive member 214 to thereby occlude the vessel 212.

In the example of urethral occlusion only, the pulley 268 in its resting state is biased so that the occlusive member 214 can apply approximately 0 to 20 cm $H_2O$ pressure to the urethra. Such a pressure range has been known to be adequate to prevent urinary leakage during normal, less stressful activities. It will be appreciated that lesser and higher pressures may be employed depending on the particular user. Urethral pressure can be continuously or intermittently monitored by the pressure sensing element 298. The pressure sending element 298 can be situated between the occlusive member 214 and the outer surface of the vessel 212 or urethra in this case. Abdominal or bladder pressure is monitored continuously or intermittently by the pressure sensor 299 which is implanted, for example within any of the abdominal cavity, the abdominal wall, the bladder, or the bladder wall.

As bladder filling occurs, bladder pressure increases for example within the range of approximately 20-60 cm $H_2O$. In one example of operation, the pressure sensor 299 senses this pressure increase, and signals the micro-processor based control 297 to turn the motor 295 on, and cause the pulley 268 to rotate and increase tension on the tracking suture 254 to affect a rise in urethral pressure. When the pressure sensing element 298 detects that urethral pressure is 60-80 cm $H_2O$, the motor 295 is turned off and the pulley 268 can be held in position to prevent any further pressure increase or decrease. Once the abdominal/bladder pressure reduces to 20 cm $H_2O$ or less, the pressure sensor 299 signals the micro-processor based control 297 to allow the motor 295 to reverse direction and reduce tension on the traction suture 254 until urethral pressures between 0 and 20 cm $H_2O$ are achieved. Such a configuration can provide a vessel occlusive device with automatic control.

Stressful events such as coughing, sneezing, laughing, etc. can often cause abdominal/bladder pressures spikes in excess of 60 cm $H_2O$. Pressure rise times of about 35 milliseconds (msec) and elevated pressure durations of approximately 100 msec have been recorded for such events. Sensing such pressure levels, the micro-processor based control 297 in operation can cause the motor 295 to turn on and can rotate the pulley 268 to affect a rise in urethral pressure. For example, the urethral pressure can rise as high as approximately 120 cm $H_2O$. When abdominal/bladder pressure declines to approximately 20 cm $H_2O$ or less, the micro-processor based control 297 allows the motor 295 to reverse direction and reduce tension on the traction sutures 254 until urethral pressures between approximately 0 and 20 cm $H_2O$ are achieved.

When the user wishes to void urine, the micro-processor based control can include a switch 291 that can be manually activated through the skin. It will be appreciated that a variety of implementations of electromechanical levers, buttons, and the like may be employed on or operatively connected to the micro-processor based control 297. It further will be appreciated that the switch 291 may be a wired or wireless electrical switch. By activating the switch 291, the pulley 268 for example can be caused to free-wheel, thereby reducing tension on the traction suture 254 until approximately between 0 and 20 cm $H_2O$ urethral pressure is achieved. The user can then void urine through the unobstructed urethra (e.g. vessel 212). The user may then be required to manually activate the switch again to return the device 210 to its resting or occlusive mode. In other embodiments, the device can be suitably programmed to automatically return to its resting or occlusive mode, such as within 3-5 minutes.

As described, any of the vessel occlusive devices can be implanted in both males and females. For example, a vessel occlusive device 10 in FIG. 1 designed for implantation in males can be implanted through a single perineal or peno-scrotal incision. The occlusive member 14 can be implanted in an open, non-occluding position and stay in a deactivated state for six weeks. This helps facilitate healing and allows pain and edema to subside. Following this deactivation period, the urologist activates the device by depressing an activation lever 82 through the intact scrotal skin. In so doing, the occlusive member 14 contracts to apply a preset occlusive pressure of 60-70 cm $H_2O$ to the urethra. The patient is then free to depress the plunger 72 to release the tension of the occlusive member 14 and allow unobstructed voiding. The patient may hold the plunger 72 in the depressed position during voiding or lock the plunger 72 in a deactivated state for voiding or nocturnal deactivation. To re-establish urethral occlusive pressure and continence, the patient releases the plunger 72 or pushes the activation lever 82.

For females, any of the occlusive devices can be implanted through a transvaginal or abdominal incision and employing similar deactivation/activation procedures as with males. Any of the occlusive members can be disposed to encircle the bladder neck or mid-urethra. Any of the control mechanisms can be miniaturized for female implantation in the labia or abdominal skin, where it could be operated by manual depression of a plunger such as through the labial or abdominal tissue.

Another benefit of the vessel occlusive devices described herein is that fluid loss will not render the device inoperative. For example, other artificial urinary sphincter concepts are hydraulic (e.g. bias applied to the urethra through a pressurized balloon). When a leak develops, devices employing such concepts become inoperative since the balloon is no longer pressurized. The inventive concepts described herein may allow fluid to leave an occlusive device without affecting its function.

With reference to FIG. 11, in preparation for implantation, the vessel occlusive device 110 of FIG. 2A may be filled with one or more of many solutions intended to replace air in open spaces within the device and/or provide a therapeutic effect. Such solutions 133 can include, but are not limited to, isotonic saline, antibiotics, anti-inflammatory drugs such as dexamethasone, and anti-proliferative drugs such as rapamycin. Antibiotics also may be used to combat post-operative infections which may occur following implantation procedures. Anti-inflammatory and anti-proliferative drugs also may be used to moderate the formation of the tissue capsule forming around implanted devices which sometimes interfere with their function.

The vessel occlusive device 110 may be filled with therapeutic solutions using for example a syringe 400. The therapeutic solution can be delivered to surrounding tissues over time. As shown, the control mechanism 116 in one embodiment is encapsulated by a silicone rubber boot 164 which offers an integral rubber needle puncture septum 166. As a solution(s) fills the control mechanism 116, it can wick towards and through the porous structure of the occlusive member 114. When droplets of solution appear on the surface of the pliable region 118 of the occlusive member 114, the device 110 has been fully filled and the needle is withdrawn from the septum 166. Once the device is implanted, the solutions can continue to elute passively from the occlusive member 114 into the surrounding tissue to provide their therapeutic effect. It will be appreciated that solutions may also be refilled as needed, so that the device can provide for extended and/or indefinite elution. It also will be appreciated that solutions can be infused into the device 110, if required due to infection or tissue capsule growth, by accessing the septum 166 with a needle through the user's skin and so that the device need not be removed.

In one embodiment, the occlusive member 114 as described has a micro-porous construction intended to minimize tissue in-growth, yet allow drug to elute from its surface. These drug solutions may be selected to prevent post-operative infections and/or minimize pseudo-capsular formation which may inhibit the contraction or expansion of the occlusive member 114.

It is to be understood that the above detailed description is intended to be illustrative, and not restrictive. Other embodiments, including any process of using a thermoplastic medium for imprinting a print and in turn making a personalized ornamental article, will be apparent to those of skill in the art upon reading and understanding the above description. The scope of the invention should, therefore, be determined with reference to the appended claims, along with the full scope of equivalents to which such claims are entitled.

What is claimed is:

1. An apparatus for occluding a fluid conveying vessel in a body, comprising:
    an occlusive member having proximate and distal ends, the occlusive member including a conduit region proximately disposed toward the proximate end and a pliable region proximately disposed toward the distal end, the occlusive member being actuatable to an occluding position and actuatable to a non-occluding position where an occlusive force is respectively transmitted to and released from the occlusive member, and where the pliable region is configured to at least partially encircle the vessel and is configured to exert an occluding pressure on the vessel, when the occlusive force is transmitted through the conduit region; and
    a control mechanism connected to the conduit region of the occlusive member, the control mechanism is configured to actuate the occlusive member into the occluding position and actuate the occlusive member into the non-occluding position,
    wherein the occlusive member comprises an inner extrusion covered by an outer extrusion, the inner and outer extrusions being porous, where the outer extrusion is less porous than the inner extrusion.

2. The apparatus of claim 1, further comprising a clip disposed on the distal end of the occlusive member and an attachment portion disposed between the proximate and distal ends of the occlusive member, the attachment portion including a band configured to connect to the clip, such that the pliable region is formed generally as a circle.

3. The apparatus of claim 2, further comprising tabs proximately attached to the distal end, the tabs configured to facilitate connection of the clip to the band.

4. The apparatus of claim 1, wherein the occlusive member is configured as a sling.

5. The apparatus of claim 1, wherein the occlusive member comprises at least one suture lumen extending from the proximate end to the distal end, and a traction suture connected to the control mechanism and extending through the suture lumen, the control mechanism configured to actuate the traction suture into the occluding position and to actuate the traction suture into the non-occluding position.

6. The apparatus of claim 1, wherein the conduit region having a higher stiffness than the pliable region.

7. The apparatus of claim 6, where the conduit region includes a lumen and a wire coil disposed through the lumen of the conduit region.

8. The apparatus of claim 1, wherein the control mechanism comprises a cable and pulley system and a plunger configured to activate and deactivate the cable and pulley system.

9. The apparatus of claim 8, wherein the cable and pulley system having a pulley with a radiused base and the cable disposed on the radiused base.

10. The apparatus of claim 1, wherein the control mechanism comprises a gear and pulley system and a plunger configured to activate and deactivate the gear and pulley system.

11. The apparatus of claim 1, further comprising a boot that covers the control mechanism.

12. The apparatus of claim 11, wherein the boot includes a septum configured for introducing at least one fluid into the control mechanism and the occlusive member, the occlusive member being configured to passively elute the fluid introduced.

13. The apparatus of claim 12, wherein the fluid includes at least one of a solution to replace air space within the control mechanism and occlusive member and a solution to provide a therapeutic effect.

14. The apparatus of claim 1, wherein the control mechanism comprises a lock, the lock configured to hold the occlusive member in the non-occluding position when the lock is activated.

15. The apparatus of claim 1, wherein the occlusive member and the control mechanism are configured for implantation into a human subject, are constructed and arranged to initially be in the occluding position when implanted, and are actuatable to release compression of the vessel to the non-occluding position.

16. A method for controlling fluid flow in a fluid conveying body vessel, comprising:
    implanting a vessel occlusive device inside the body of a subject in need of controlled fluid flow through a fluid conveying vessel, the step of implanting comprises surrounding at least a portion of the fluid conveying vessel, actuating the vessel occlusive device into a biased occluding position and applying an occlusive force to occlude the fluid conveying vessel;
    releasing the occlusive force applied to the fluid conveying vessel when fluid flow is to be allowed through the fluid conveying vessel, the step of releasing occlusive force comprises actuating the vessel occlusive device away from the biased occluding position to a non-occluding position;
    reactuating the vessel occlusive device into the biased occluding position when fluid flow is no longer to be allowed; and
    passively eluting at least one solution from the vessel occlusive device into the body, the solution comprising a solution to provide a therapeutic effect when eluted.

17. The method of claim 16, further comprising applying a constant force on the fluid conveying vessel during at least one of the implanting and the reactuating steps.

18. The method of claim 16, wherein the step of releasing the occlusive force applied to the fluid conveying vessel comprises locking the vessel occlusive device in the non-occluding position.

19. An apparatus for occluding a fluid conveying vessel in a body, comprising:
    an occlusive member having proximate and distal ends, the occlusive member including a conduit region proximately disposed toward the proximate end and a pliable region proximately disposed toward the distal end, the occlusive member being actuatable to an occluding position and actuatable to a non-occluding position where an occlusive force is respectively transmitted to and released from the occlusive member, and where the pliable region is configured to at least partially encircle the vessel and is configured to exert an occluding pressure on the vessel, when the occlusive force is transmitted through the conduit region;
    a control mechanism connected to the conduit region of the occlusive member, the control mechanism is configured to actuate the occlusive member into the occluding position and actuate the occlusive member into the non-occluding position; and
    a boot that covers the control mechanism, the boot includes a septum configured for introducing at least one fluid into the control mechanism and the occlusive member, the occlusive member being configured to passively elute the fluid introduced.

* * * * *